(12) United States Patent
Martino et al.

(10) Patent No.: US 9,204,821 B2
(45) Date of Patent: Dec. 8, 2015

(54) METHOD OF AND APPARATUS FOR DETECTING UPPER RESPIRATORY BACTERIAL INFECTION FROM EXHALED MAMMALIAN BREATH AND COLORIMETRIC SENSOR ARRAY CARTRIDGE

(75) Inventors: Raymond Anthony Martino, Los Gatos, CA (US); Sung Hyun Lim, Mountain View, CA (US); Paul A. Rhodes, Woodside, CA (US)

(73) Assignee: ISENSE MEDICAL CORP., West Palm Beach, FL (US)

( * ) Notice: Subject to any disclaimer, the term of this patent is extended or adjusted under 35 U.S.C. 154(b) by 591 days.

(21) Appl. No.: 13/467,366

(22) Filed: May 9, 2012

(65) Prior Publication Data

US 2013/0303929 A1  Nov. 14, 2013

(51) Int. Cl.
*A61B 5/08* (2006.01)
*A61B 5/097* (2006.01)
*G01N 33/497* (2006.01)

(52) U.S. Cl.
CPC ............... *A61B 5/097* (2013.01); *A61B 5/082* (2013.01); *G01N 33/497* (2013.01)

(58) Field of Classification Search
CPC ....... A61B 5/082; A61B 5/097; G01N 33/497
USPC ............... 600/529, 532, 534; 73/23.2–23.36
See application file for complete search history.

(56) References Cited

U.S. PATENT DOCUMENTS

| | | | |
|---|---|---|---|
| 4,539,181 A | 9/1985 | Westrup | |
| 5,807,701 A | 9/1998 | Payne et al. | |
| 5,996,586 A | 12/1999 | Phillips | |
| 6,190,858 B1 | 2/2001 | Persaud et al. | |
| 6,368,558 B1 | 4/2002 | Suslick et al. | |
| 6,495,102 B1 | 12/2002 | Suslick | |
| 6,627,394 B2 | 9/2003 | Kritzman et al. | |
| 6,841,391 B2 | 1/2005 | Lewis et al. | |
| 7,129,554 B2 | 10/2006 | Lieber et al. | |
| 7,255,677 B2 | 8/2007 | Burch et al. | |
| 7,261,857 B2 | 8/2007 | Suslick | |
| 7,977,054 B2 | 7/2011 | Johnson, Jr. et al. | |
| 2003/0143112 A1 | 7/2003 | Suslick | |
| 2003/0166298 A1 | 9/2003 | Suslick | |

(Continued)

OTHER PUBLICATIONS

Chromic Acid, OChemPal, 2009.*

(Continued)

*Primary Examiner* — Jacqueline Cheng
*Assistant Examiner* — Puya Agahi
(74) *Attorney, Agent, or Firm* — Kirschstein, et al.

(57) ABSTRACT

An upper respiratory bacterial infection is detected from exhaled mammalian breath by using a colorimetric sensor array having a spectral response characteristic that changes when exposed to bacteria-produced analytes in the exhaled breath. A flow regulating system directs a leading portion of the exhaled breath into gaseous communication with the array to change its spectral response characteristic, and discharges a trailing portion of the exhaled breath exteriorly of the apparatus. A spectral analysis system analyzes the spectral response characteristic changed solely by the leading portion of the exhaled breath, and detects the upper respiratory bacterial infection when the bacteria-produced analytes are present therein. Reactivity of the analytes with the array is increased by advance oxidizing and/or heating the analytes.

18 Claims, 3 Drawing Sheets

(56) References Cited

U.S. PATENT DOCUMENTS

| | | | |
|---|---|---|---|
| 2005/0171449 A1 | 8/2005 | Suslick | |
| 2005/0177056 A1* | 8/2005 | Giron et al. | 600/543 |
| 2006/0051733 A1* | 3/2006 | Lowe et al. | 435/4 |
| 2008/0050839 A1 | 2/2008 | Suslick et al. | |
| 2008/0199904 A1 | 8/2008 | Suslick et al. | |
| 2009/0239252 A1 | 9/2009 | Trevejo et al. | |
| 2010/0081955 A1* | 4/2010 | Wood et al. | 600/532 |
| 2010/0166604 A1 | 7/2010 | Lim et al. | |
| 2010/0291617 A1 | 11/2010 | Trevejo et al. | |

OTHER PUBLICATIONS

Cerry D, H.E., Woodwell D, Rechtsteiner E, National Ambulatory Medical Care Survey: 2006 Summary. CDC National Heath Statistics Report, 2008.

Anon, J.B., et al., Antimicrobial treatment guidelines for acute bacterial rhinosinusitis. Otolaryngol Head Neck Surg, 2004. 130(1 Suppl): p. 1-45.

Sharp, H.J., et al., Treatment of acute and chronic rhinosinusitis in the United States, 1999-2002. Arch Otolaryngol Head Neck Surg, 2007. 133(3): p. 260-5.

Lai, S.Y., et al., Identification of upper respiratory bacterial pathogens with the electronic nose. Laryngoscope, 2002. 112(6): p. 975-979.

Dosh, S.A., et al., Predictors of antibiotic prescribing for nonspecific upper respiratory infections, acute bronchitis, and acute sinusitis. An UPRNet study. Upper Peninsula Research Network. J Fam Pract, 2000. 49(5): p. 407-14.

Thaler ER, L.D., Hanson CW, Diagnosis of rhinosinusitis with a colorimetric sensor array. J. Breath Res., 2008. 2: p. 4.

Gwaltney, J.M., Jr., et al., Computed tomographic study of the common cold. N Engl J Med, 1994. 330(1): p. 25-30.

Hickner, J.M., et al., Principles of appropriate antibiotic use for acute rhinosinusitis in adults: background. Ann Intern Med, 2001. 134(6): p. 498-505.

Carey, J.R., et al., Rapid Identification of Bacteria with a Disposable Colorimetric Sensing Array. Journal of the American Chemical Society. 133(19): p. 7571-7576.

Sande, M.A. and J.M. Gwaltney, Acute community-acquired bacterial sinusitis: continuing challenges and current management. Clin Infect Dis, 2004. 39 Suppl 3: p. S151-58.

Hamilton-Kemp, T., et al., Production of the long-chain alcohols octanol, decanol, and dodecanol by *Escherichia coli*. Current Microbiology, 2005. 51(2): p. 82-86.

Scotter, J.M., et al., The rapid evaluation of bacterial growth in blood cultures by selected ion flow tube-mass spectrometry (SIFT-MS) and comparison with the BacT/Alert automated blood culture system. Journal of Microbiological Methods, 2006. 65(3): p. 628-631.

Maddula, S., et al., Detection of volatile metabolites of *Escherichia coli* by multi capillary column coupled ion mobility spectrometry. Analytical and Bioanalytical Chemistry, 2009. 394(3): p. 791-800.

Zechman, J.M., S. Aldinger, and J.N. Labows, Characterization of Pathogenic Bacteria by Automated Headspace Concentration Gas-Chromatography. Journal of Chromatography, 1986. 377: p. 49-57.

Preti, G., et al., Volatile compounds characteristic of sinus-related bacteria and infected sinus mucus: Analysis by solid-phase microextraction and gas chromatography-mass spectrometry. Journal of Chromatography B-Analytical Technologies in the Biomedical and Life Sciences, 2009. 877(22): p. 2011-2018.

Zechman, J.M. and J.N. Labows, Volatiles of Pseudomonas-Aeruginosa and Related Species by Automated Headspace Concentration—Gas-Chromatography. Canadian Journal of Microbiology, 1985. 31(3): p. 232-237.

Rakow, N.A. and K.S. Suslick, A colorimetric sensor array for odour visualization. Nature, 2000. 406: p. 710-713.

Suslick, K.S., et al., Seeing smells: development of an optoelectronic nose. Quimica Nova, 2007. 30: p. 677-681.

Suslick, B.A., L. Feng, and K.S. Suslick, Discrimination of Complex Mixtures by a Colorimetric Sensor Array: Coffee Aromas. Anal. Chem., 2010. 82(5): p. 2067-2073.

Suslick, K.S., N.A. Rakow, and A. Sen, Colorimetric sensor arrays for molecular recognition. Tetrahedron, 2004. 60 (49): p. 11133-11138.

Feng, L., et al., A colorimetric sensor array for identification of toxic gases below permissible exposure limits. Chem. Comm., 2010. 46(12): p. 2037-2039.

Feng, L., C.J. Musto, and K.S. Suslick, A Simple and Highly Sensitive Colorimetric Detection Method for Gaseous Formaldehyde. J. Am. Chem. Soc., 2010. 132(12): p. 4046-4047.

Lim, S.H., et al., An optoelectronic nose for the detection of toxic gases. Nature Chemistry, 2009. 1(7): p. 562-567.

Lim, S.H., et al., A colorimetric sensor array of porous pigments. Analyst, 2009. 134(12): p. 2453-2457.

Color tunable, ratiometric pH sensor for high and low pH values base on 9-(cycloheptatrienylidene)fluorene derivatives, Guorong Zheng, et al., ScienceDirect, Sensors and Actuators B 122 (2007) 389-394.

Acidic-sensing property of 9-(cycloheptatrienylidene)fluorene by UV-Vis spectroscopy, Zixing Wang, et al., ScienceDirect, Sensors and Actuators B 99 (2004) 264-266.

Development of a novel hand-held toluene gas sensor: Possible use in the prevention and control of sick building syndrome, Koji Kawamura, et al., ScienceDirect, Measurement 39 (2006) 490-496.

Gas Phase Sensors for Bases Using Rhodamine B in Nafion Films, Eunhae Hwang, et al., Published online Jan. 14, 2010, Wiley InterScience (222.interscience.wiley.com), 2425-2432.

Organic Reactions in a Solid Matrix—V+, Silica-Gel Supported Chromic Acid Reagents+, R. P. Singh, et al., Tetrahedron vol. 35, pp. 1789-1793, Pergamon Press Ltd. 1979.

\* cited by examiner

METHOD OF AND APPARATUS FOR DETECTING UPPER RESPIRATORY BACTERIAL INFECTION FROM EXHALED MAMMALIAN BREATH AND COLORIMETRIC SENSOR ARRAY CARTRIDGE

FIELD OF THE DISCLOSURE

The present disclosure relates generally to a method of, and an apparatus for, detecting an upper respiratory bacterial infection by recognizing bacterial biomarkers in exhaled mammalian breath and, more particularly, to enhancing the sensitivity and accuracy of such detection, especially at medically relevant concentrations, and, still more particularly, to an improved colorimetric sensor array cartridge for detecting bacterial biomarkers.

BACKGROUND

Upper respiratory infections (URIs) include rhinitis, pharyngitis/tonsillitis and laryngitis, and their complications such as sinusitis and ear infection, and are the leading reported reason for primary care physician office visits in the United States. Over two-hundred different viruses have been isolated for URI patients, the most common virus being the rhinovirus. URI cases may also be caused by bacteria, the most common virus being the Group A *streptococcus* in streptococcal pharyngitis ("strep throat").

It is important for primary care physicians to determine whether URI cases are viral or bacterial, because, among other things, a bacterial URI patient can be treated with an antibiotic, whereas an antibiotic is ineffective against a viral URI. One complicating factor is that the physician cannot reliably rely on clinical judgment alone since the signs and symptoms of bacterial and viral URI are similar. Therefore, according to current medical practice, the physician typically sends a swabbed specimen from the patient to a laboratory for culturing over a two or three day waiting period, after which the culture is examined by a specialist for a determination whether the culture is viral or bacterial. Due to this delay, many physicians will also automatically prescribe an antibiotic as an advance precautionary treatment in the event that the URI later proves to be bacterial. The associated extra expense and delay not only has financial and personal cost, but also leads to the overuse of antibiotics, antibiotic resistance, and longer and more severe illnesses and, sometimes, to additional primary care and specialist office visits.

It is known that metabolic growth products from bacteria, as they proliferate, produce unique volatile organic compounds (VOCs), also known as analytes, that are released into the air exhaled by a patient's respiratory system. Different bacteria, even different strains of bacteria, produce distinct profiles of analytes, such as amines, sulfides, and carboxylic acids. For example, according to medical reports, *Staphylococcus aureus* may produce isovaleric acid, butyric acid and/or ammonia; *Pseudomonas aeruginosa* may emit dimethylsulfide, 2-aminoacetophenone, and/or dimethylpyrazine; and *E. coli* may produce acetic acid in a glucose-rich media and/or amines in a protein-rich media. These unique analytes or metabolites produce biomarkers or "signatures" in the patient's exhaled breath that can be recognized by vapor analysis.

Vapor analysis has been used for detecting and differentiating chemically diverse analytes by passing a patient's exhaled breath over a colorimetric sensor array having multiple sensors, each constituting a chemoresponsive soluble dye or an insoluble pigment. Examples of such colorimetric sensor arrays are disclosed in U.S. Pat. No. 6,368,558; U.S. Pat. No. 6,495,102; U.S. Pat. No. 7,261,857; U.S. Patent Publication No. 2008/0050839; and U.S. Patent Publication No. 2010/0166604. One sensor can respond to many analytes, and many sensors can respond to any given analyte. A distinct pattern of color responses produced by the colorimetric sensor array provides a characteristic signature for each analyte, and such color response patterns have been used to diagnose various diseases, such as lung cancer, as disclosed, for example, in U.S. Pat. No. 6,319,724; U.S. Patent Publication No. 2010/0191474; International Publication No. WO 2010/079491; and Mazzone et al., "*Diagnosis of lung cancer by the analysis of exhaled breath with a colorimetric sensor array*," Thorax 2007; 62:565-568.

As advantageous as such colorimetric sensor arrays have been in detecting analytes and in diagnosing diseases, such as lung cancer, they have not proven to be altogether satisfactory. In particular, existing colorimetric sensor arrays may not detect some reported bacteria biomarkers, analytes and other disease signatures in exhaled breath, or may not detect some reported bacteria biomarkers, analytes and signatures at medically relevant concentrations, e.g., below 100 parts per billion (ppb), due to the low reactivity of the analytes with the dyes and pigments used in existing colorimetric sensor arrays. Such analytes include, but are not limited to, esters, ketones, alcohols, alkenes, and/or hydrocarbons.

Accordingly, a non-invasive, simple, cost-efficient, accurate, and sensitive at medically relevant concentrations, method of, and apparatus for, rapidly diagnosing upper respiratory bacterial infections, that is capable of providing real-time results in the context of a single visit to a physician's office, are needed. Also needed is an improved colorimetric sensor array that can detect not only upper respiratory bacterial infections, but also bacteria in general, especially bacteria associated with other diseases and medical and/or sanitary conditions, whether or not in exhaled breath.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
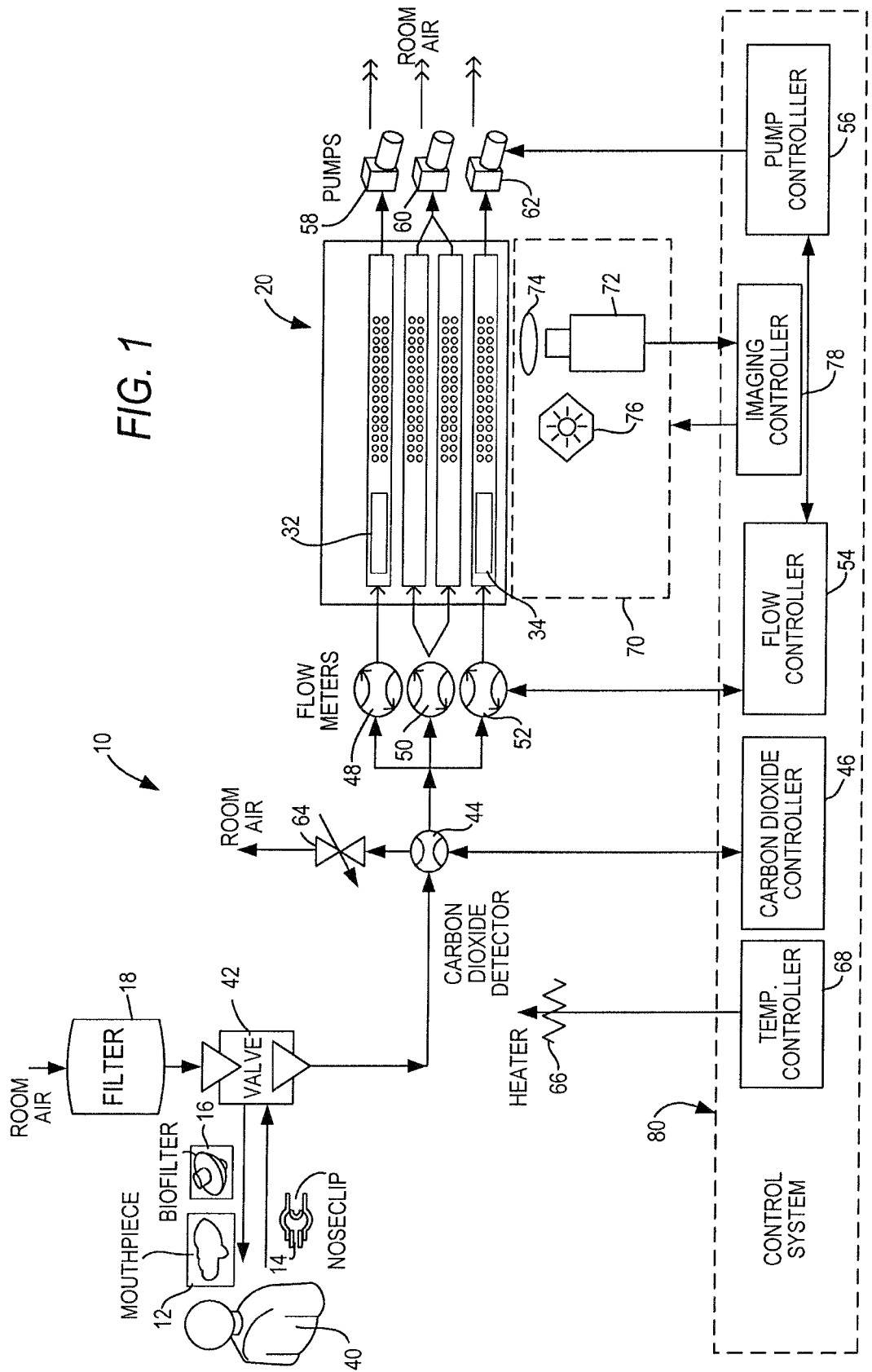
FIG. 1 is a block diagram of an apparatus for diagnosing upper respiratory bacterial infections in accordance with the method of this invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

An apparatus, in accordance with one feature of this invention, is operative for detecting an upper respiratory bacterial infection from exhaled mammalian breath. The apparatus includes a colorimetric sensor array having a spectral response characteristic that changes when exposed to bacteria-produced analytes in the exhaled mammalian breath. For example, the array has a plurality of chemoresponsive sensors or colorants that change color when exposed to the bacteria-produced analytes. The apparatus also includes a flow regulating system for directing a leading portion of the exhaled mammalian breath, especially a predetermined volume or quantity thereof, into gaseous communication with the colorimetric sensor array, especially at a predetermined flow rate, to change the spectral response characteristic, and for discharging a trailing portion of the exhaled mammalian breath away from gaseous communication with the colorimetric sensor array exteriorly of the apparatus. A spectral analysis system analyzes the spectral response characteristic changed solely by the leading portion of the exhaled mammalian breath, and detects the upper respiratory bacterial infection when the bacteria-produced analytes are present therein.

Preferably, the colorimetric sensor array has a plurality of separate flow channels in which the chemoresponsive colorants are located, preferably at downstream portions of the channels. In order to increase the reactivity of the bacteria-produced analytes with the chemoresponsive colorants in at least one of the channels, an oxidizer, e.g., sulfochromic acid or iodine pentoxide, is provided at an upstream portion of the one channel for oxidizing the bacteria-produced analytes. Different oxidizers may be used in different channels. Instead of using an oxidizer, a heater may be used for heating the bacteria-produced analytes at an upstream portion of the one channel, thereby increasing the reactivity of the bacteria-produced analytes with the chemoresponsive colorants in the one channel.

Increased sensitivity and accuracy for identifying bacteria-produced analytes in exhaled breath, especially bacteria associated with URIs are thus assured not only by the increased reactivity enabled by the oxidizers and/or the heater, but also by analyzing only the leading portion of the exhaled mammalian breath. During an exhalation or breath cycle, the level of carbon dioxide rapidly increases along a steep slope at the start of the exhalation (i.e., the "leading portion" of the exhaled breath) until the alveolar plateau is reached where the carbon dioxide level increases much more slowly along a gradual, almost horizontal, slope at the end of the exhalation (i.e., the "trailing portion" of the exhaled breath). The bacteria associated with URIs are best recognized by only using the leading portion of the exhaled mammalian breath where the carbon dioxide rapidly increases along the steep slope.

In accordance with another feature of this invention, the colorimetric sensor array may be used not only to detect upper respiratory bacterial infections, as described above, but also bacteria in general, especially bacteria associated with other diseases and medical and/or sanitary conditions, whether or not in exhaled breath. For example, bacteria from deep lung infections, as is often the case for tuberculosis, may be detected by the colorimetric sensor array by sampling a predetermined quantity of the trailing portion of the exhaled breath that is directed through the array at a predetermined flow rate. Other respiratory diseases can also be detected, again by sampling a predetermined quantity of the exhaled breath in a portion of the breath cycle, and by directing the sampled quantity at a predetermined flow rate through the array. The bacteria need not be entrained in exhaled breath, but, for example, can be entrained in a carrier gas that is passed through medical equipment whose sanitary condition is to be determined.

Turning now to the drawings, reference numeral 10 in FIG. 1 generally identifies an apparatus for detecting an upper respiratory bacterial infection from exhaled mammalian breath. The apparatus 10 includes a colorimetric sensor array cartridge 20 (shown in isolation in FIGS. 2-3) having a plurality of chemoresponsive sensors or colorants whose spectral response characteristic changes when exposed to bacteria-produced analytes in the exhaled mammalian breath. As used herein, the term "colorant" means any material that absorbs and/or scatters and/or reflects and/or emits light when exposed to higher frequency electromagnetic radiation, including ultraviolet light, infrared light and visible light. The term "chemoresponsive colorant" means a colorant that undergoes a change in spectral properties in response to a change in its chemical environment by exposure to the analytes. The term "change in spectral properties" of a colorant means a change in the frequency and/or intensity of the light the colorant absorbs and/or scatters and/or reflects and/or emits. The term "dye" means a soluble colorant. The term "pigment" means an insoluble colorant.

Figure 2:
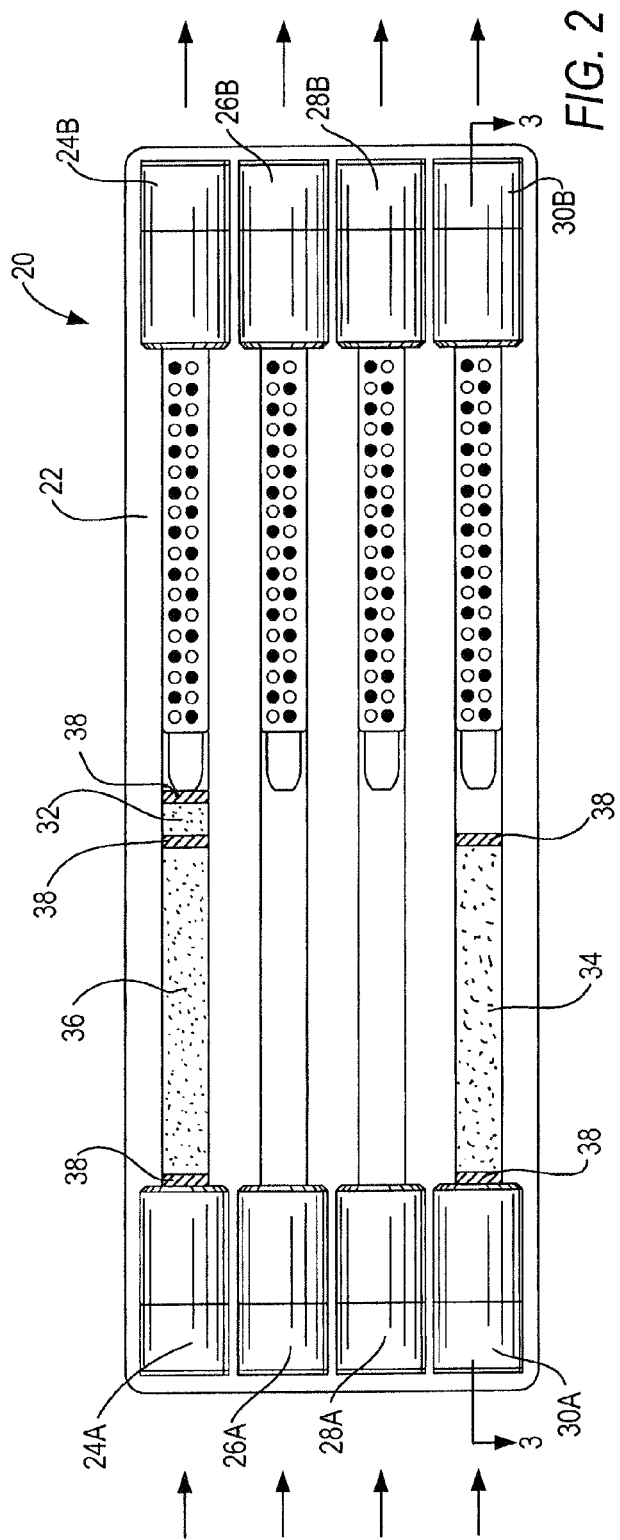
FIG. 2 is a top plan view of a colorimetric sensor array cartridge used in the apparatus of FIG. 1.
Figure 3:
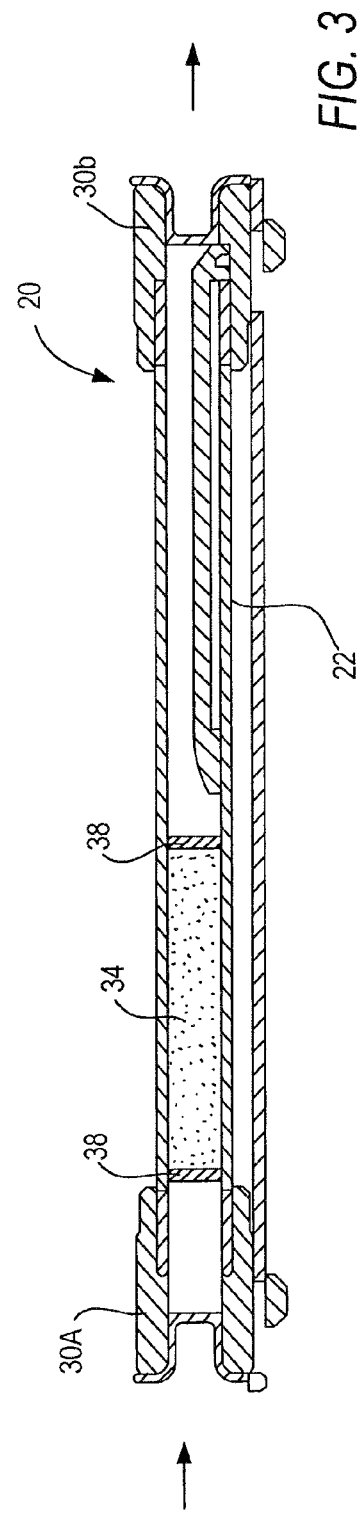
FIG. 3 is a sectional view of the colorimetric sensor array cartridge taken on line 3-3 of FIG. 2.

The cartridge 20 includes a substrate 22 on which the chemoresponsive colorants are deposited, e.g., by ink jet printing, preferably in a pattern of rows and columns. The colorants are shown in FIGS. 2-3 as generally circular spots arranged in four separate flow channels, with a 2×18 array of colorants in each channel. The spots need not be circular, and the number of flow channels may be other than four. Each array may have a different number of rows and columns than those illustrated. A first channel extends from an inlet 24A to an outlet 24B. A second channel extends from an inlet 26A to an outlet 26B. A third channel extends from an inlet 28A to an outlet 28B. A fourth channel extends from an inlet 30A to an outlet 30B. The substrate 22 may be any material that can retain such spots on its surface, preferably without leaching. Examples of substrates 22 include polymeric membranes, such as cellulose acetate or polyvinylidene difluoride (PVDF); nonporous surfaces, such as glass or metal; and nonporous surfaces, such as poly(tetrafluoroethylene) (PTFE) or poly(ethylene terephthalate) (PET).

The colorants listed in the following Table 1 may advantageously be used:

TABLE 1

| No. | COLORANT |
|---|---|
| 1 | 5,10,15,20-Tetraphenyl-21H,23H-porphine zinc |
| 2 | 5,10,15,20-Tetraphenyl-21H,23H-porphine copper(II) |
| 3 | 5,10,15,20-Tetraphenyl-21H,23H-porphine manganese(III) chloride |
| 4 | 2,3,7,8,12,13,17,18-Octaethyl-21H,23H-porphine iron(III) chloride |
| 5 | 5,10,15,20-Tetraphenyl-21H,23H-porphine cobalt(II) |
| 6 | meso-Tetra(2,4,6-trimethylphenyl)porphine |
| 7 | Nitrazine Yellow (basic) |
| 8 | Methyl Red (basic) |
| 9 | Chlorophenol Red (basic) |
| 10 | Napthyl Blue Black |
| 11 | Bromothymol Blue (basic) |
| 12 | Thymol Blue (basic) |
| 13 | m-Cresol purple (basic) |
| 14 | Zinc (II) Acetate with m-Cresol purple (basic) |
| 15 | Mercury (II) Chloride with Bromophenol Blue (basic) |
| 16 | Mercury (II) Chloride with Bromocresol Green (basic) |

TABLE 1-continued

| No. | COLORANT |
|---|---|
| 17 | Lead (II) Acetate |
| 18 | Tetraiodophenolsulfonephthalein |
| 19 | Fluorescein |
| 20 | Bromocresol Green |
| 21 | Methyl Red |
| 22 | Bromocresol Purple |
| 23 | Bromophenol Red |
| 24 | Brilliant Yellow |
| 25 | Silver nitrate + Bromophenol Blue (basic) |
| 26 | Silver nitrate + Bromocresol Green (basic) |
| 27 | Cresol Red (acidic) |
| 28 | Disperse Orange 25 |
| 29 | m-Cresol Purple |
| 30 | Nitrazine Yellow |
| 31 | Cresol Red |
| 32 | Bromocresol Green |
| 33 | Phenol Red |
| 34 | Thymol Blue |
| 35 | Bromophenol Blue |
| 36 | Nile Red |

As also shown in FIG. 2, the colorants in at least one channel and, as illustrated, in each channel are deposited, e.g., by ink jet printing, at a downstream portion of each channel closely adjacent its respective outlet 24B, 26B, 28B, 30B. As described below in connection with FIG. 4, it is a leading portion of the exhaled mammalian breath that is directed into gaseous communication with the colorants in each channel to change their spectral response characteristic, and it is this changed characteristic for each channel that will subsequently be analyzed to detect upper respiratory bacterial infections. In order to increase the reactivity of any analytes with the colorants, an oxidizer 32 and/or 34, e.g., sulfochromic acid or iodine pentoxide, is provided at an upstream portion of at least one channel and, as illustrated, two of the channels, for oxidizing the analytes prior to being brought into gaseous communication with the colorants in the respective channel. Different oxidizers may be used in different channels. Thus, a high strength oxidizer 32 is provided in the first channel, and a different low strength oxidizer 34 is provided in the fourth channel. Oxidizers are not present in the second and third channels.

As also shown in FIG. 2, a desiccant 36 is located in the first channel to dry the leading portion of the exhaled breath prior to oxidation by the oxidizer 32. A desiccant could also be used in any of the other channels. A plurality of wire mesh retainers 38 is used to retain the desiccant 36 and/or the oxidizers 32, 34 in place within their respective channels.

Returning to FIG. 1, the apparatus 10 includes a mouthpiece 12 or other structure into which a subject 40 exhales a breath, into an air tube, e.g., similar to an alcohol breathalyzer, or container which can capture volatile gaseous components in the subject's exhaled breath. A noseclip 14 can be employed to insure that inhalation and exhalation are performed through the subject's mouth. A biofilter 16 removes bacteria from the exhaled breath to prevent bacterial contamination. A charcoal filter 18 filters the incoming ambient air during inhalation. A T-valve 42 directs the ambient through the biofilter 16 to the subject 40 during inhalation, and also directs the exhaled air to a carbon dioxide detector 44 during exhalation. The mouthpiece 12, the noseclip 14, the air tube and the T-valve 42 are preferably made of a medical grade plastic capable of being sterilized and are optionally disposable.

Figure 4:
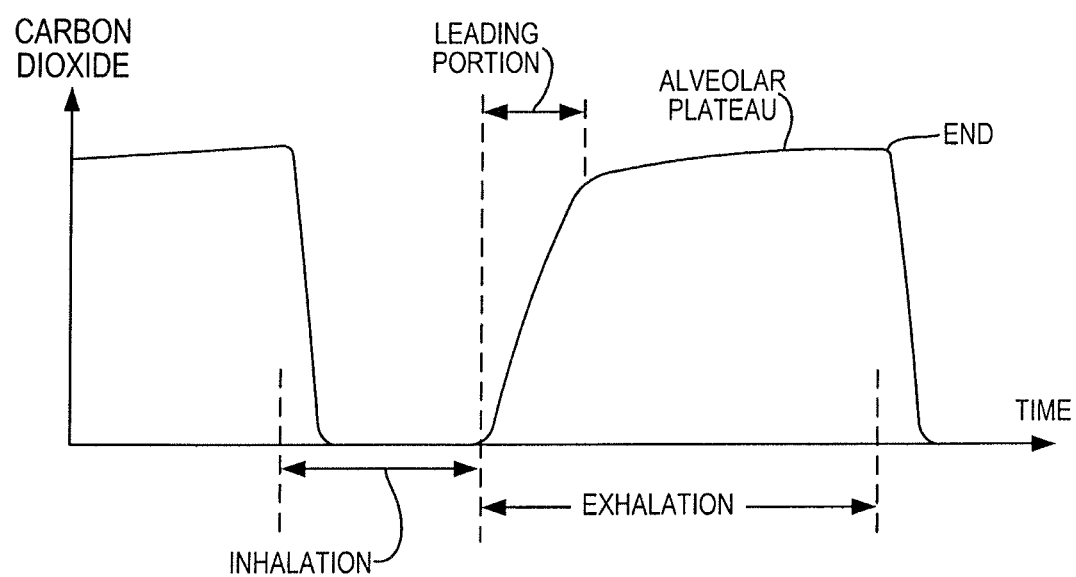
FIG. 4 is a graph of exhaled carbon dioxide versus time of a breath to be analyzed by the apparatus of FIG. 1.

Operation of the carbon dioxide detector 44 and its controller 46 are best described in connection with the graph of FIG. 4, which depicts the level of carbon dioxide over time during a breath cycle. During an inhalation, the level of carbon dioxide rapidly decreases, but during an exhalation, the level of carbon dioxide in the exhaled breath rapidly increases along a steep slope at the start of the exhalation (the "leading portion") until the alveolar plateau is reached where the carbon dioxide level increases much more slowly along a gradual, almost horizontal, slope at the end of the exhalation (the "trailing portion"). As described above, the bacteria associated with URIs are best recognized by only using the leading portion of the exhaled breath where the carbon dioxide rapidly increases along the illustrated steep slope.

The carbon dioxide detector 44 and its controller 46 monitor this breath cycle, and are operative for directing the leading portion of the exhaled mammalian breath to a plurality of flow meters 48, 50, 52 into gaseous communication with the colorants of the colorimetric sensor array cartridge 20 to change its spectral response characteristic, and for discharging a trailing (alveolar plateau) portion of the exhaled mammalian breath to a discharge valve 64 away from gaseous communication with the colorimetric sensor array cartridge 20 exteriorly of the apparatus into the ambient air. To insure that nasopharyngeal gas does not contaminate the exhaled breath, a small amount of flow resistance (between 5-15 cm $H_2O$) is established in the flow path to the cartridge 20 to cause the subject's soft palate to close during exhalation. If a sinus infection is suspected, then it may be preferred that the subject's soft palate not be closed.

Flow meter 48 is connected to the inlet 24A of the first channel, and a pump 58 is connected to the outlet 24B of the first channel. Flow meter 50 is connected to both inlets 26A, 28A of the second and third channels, and a pump 60 is connected to both outlets 26B, 28B of the second and third channels. Flow meter 52 is connected to the inlet 30A of the fourth channel, and a pump 62 is connected to the outlet 30B of the fourth channel. The flow meters 48, 50, 52 are controlled by a flow controller 54. The flow meters 48, 50, 52 insure that a predetermined volume or quantity of the leading portion of the exhaled breath, e.g., in a range of from about 100 milliliters to about 10 liters, especially about 1 liter, is captured by each channel. The pumps 58, 60, 62 are controlled by a pump controller 56. The pumps 58, 60, 62 insure that the captured leading portion of the exhaled breath is directed at a predetermined flow rate through the channels, e.g., in a range of from about 100 milliliters per minute to about 1 liter per minute, especially about 250 milliliters per minute. The flow meters 48, 50, 52, the pumps 58, 60, 62, the flow controller 54, and the pump controller 56 together comprise a flow regulating system operative to regulate the flow of the leading portion of the exhaled mammalian breath to, across, and past the cartridge 20 by controlling the flow rate and the flow volume over a predetermined measuring time period.

Instead of using one or more oxidizers 32, 34, one or more heaters 66 under the control of a temperature controller 68 may be used for heating the bacteria-produced analytes at an upstream portion of one or more of the channels, thereby increasing the reactivity of the bacteria-produced analytes with the chemoresponsive colorants in the respective channel. The heater 66 could also be used to maintain the apparatus at room temperature to avoid breath condensation.

A spectral analysis system 70 is operative for analyzing the spectral response characteristic changed solely by the leading portion of the exhaled mammalian breath. The spectral analysis system 70 includes an imaging or image capture component 72 (e.g., a scanner or a camera such as a charge coupled device (CCD) or a complementary metal oxide semiconductor (CMOS) device, together with an imaging lens system 74, within or external to the apparatus, for detecting, by image capture, changed responses of the colorants, e.g., dyes and/or pigments, to any bacteria-produced analytes in the exhaled breath. The system can also include an illumination source 76 to illuminate the colorants, and an imaging controller 78, preferably, a microprocessor, computer or analogous dedicated device having an operating system, logic, display, and/or data analysis capabilities. The illumination source 76 may emit light over a broad spectrum, or individual light components, such as red, blue and green light, may be successively emitted to illuminate the colorants. The illumination source 76 may also emit ultraviolet or infrared light. Alternatively, the analysis of the spectral response characteristic may be performed manually by visual inspection.

In use, the subject/patient 40 exhales breath into the flow regulating system so that only a leading portion of the exhaled breath comes in a headspace above, and flows in direct contact with, the colorants deposited on the colorimetric sensor array cartridge 20. Subsequently, the imaging component 72 captures an image of the distinct spectral (transmission, reflectance, absorption, emission) response characteristic produced by the colorants in response to any bacteria-produced analytes in the exhaled breath. The image is then processed and statistically analyzed and/or displayed by the controller 78. Analysis of the image can include comparing its entire shape against a control or reference shape over a predetermined time period, or comparing its changed response characteristic against a control or reference response characteristic at one or more times.

The controller 78, together with the other controllers 46, 54, 56, and 68, comprise a control system 80 operative for controlling all functions of the apparatus. The control system 80 is operative, among other things, for registering the starting and ending times at which exhaled breath sampling respectively commences and ends, controlling the pumps 58, 60, 62, controlling the flow meters 48, 50, 52, controlling the illumination source 76 and the imaging component 72, and processing the captured image for each channel, performing data analysis on the spectral or color changes occurring during exposure to the exhaled breath on each channel, and providing an output such as the presence or the absence of a bacterial URI. Prior to and/or during exposure to the exhaled breath, the imaging component acquires reference images for subsequent comparison. Such reference images can be captured at regular predetermined intervals and subsequently analyzed using well-known image processing techniques and algorithms to determine the presence or absence of a bacterial URI, and output the diagnosis. Such software or algorithms to achieve these tasks can be readily obtained or generated by the skilled artisan.

It has been reported in medical journals that the listed bacteria species produce the listed analytes, as set forth in the following Table 2:

TABLE 2

| BACTERIA | ANALYTES |
|---|---|
| Escherichia coli (E. coli) | octanol, decanol, dodecanol, acetaldehyde, ethanol, pentanol, acetone, hydrogen sulphide, methanethiol, indole, 2-aminoacetophenone, propene, hexane, benzaldehyde, butan-1-ol, hexan-2-one, ethanol, acetone, 2-heptanone, 2-nonanone |
| Streptococcus pneumoniae (Strep. pneumonicae) | Benzaldehyde, benzylalcohol, 2-phenylethyl alcohol, acetic acid and methyl mercaptan |

TABLE 2-continued

| BACTERIA | ANALYTES |
|---|---|
| Haemophilus influenzae (H. influenzae) | Indole, benzaldehyde, acetic acid and benzyl-alcohol |
| Branhamella (Moraxella) catarrhalis (B. cattarrhalis) | Benzaldehyde, benzylalcohol and 2-phenyl-ethyl alcohol |
| Staphylococcus aureus (Staph. aureus) | Isovaleric acid, 2-methylbutyric acid, isobutyric acid, 1-hydroxy-2-propanone, 3-hydroxy-2-butanone, butyric acid, 4-methylhexanoic acid and 2-phenylethyl alcohol |
| Pseudomonas aeruginosa (P. aeruginosa) | 2-Amino-acetophenone, dimethyldisulfide, undecene, dimethylpyrazine and dimethyl-sulfide |
| Stenotrophomonas maltophili (S. maltophilia) | Methylpyrazine, dimethylpyrazine, trimethyl-pyrazine 2-dodecane, _,_-dimethylbenzene methanol, acetophenone, 2-phenylethyl alcohol and caprolactam |
| P. perolens | Methyl mercaptan, dimethyl disulphide, dimethyl trisulphide, 3-methyl-1-butanol, butanone, 2-methoxy-3-sec-butylpyrazine |
| P. fragi | Dimethyl sulphide, dimethyl disulphide, acetaldehyde, ethyl acetate, ethanol, methyl mercaptan |
| B. fragilis, Fusobacterium sp., Veillonella sp., Clostridium sp. | Acetic acid, propionic acid, butyric acid |
| P. fluorescens, P. putrefaciens | Dimethyl disulphide, dimethyl trisulphide, methyl mercaptan, 3-methyl-1-butanol, trimethylamine |

In accordance with another feature of this invention, a method of detecting an upper respiratory bacterial infection from exhaled mammalian breath is performed by directing a leading portion of the exhaled mammalian breath into gaseous communication with a colorimetric sensor array to change a spectral response characteristic of the array when the array is exposed to bacteria-produced analytes in the exhaled mammalian breath, by discharging a trailing portion of the exhaled mammalian breath away from gaseous communication with the colorimetric sensor array, by analyzing the spectral response characteristic changed solely by the leading portion of the exhaled mammalian breath, and by detecting the upper respiratory bacterial infection when the bacteria-produced analytes are present therein.

In accordance with still another feature of this invention, a colorimetric sensor array cartridge for detecting bacteria-produced analytes, includes a substrate, a plurality of separate flow channels extending along the substrate, a plurality of chemoresponsive colorants in each channel and changing color when exposed to the analytes, and an oxidizer for oxidizing the analytes at an upstream portion of at least one of the channels to increase reactivity of the analytes with the chemo-responsive colorants located in a downstream portion of the one channel.

The colorimetric sensor array cartridge 20 may be used not only to detect upper respiratory bacterial infections, as described above, but also bacteria in general, especially bacteria associated with other diseases and medical and/or sanitary conditions, whether or not in exhaled breath. For example, bacteria from deep lung infections, as is often the case for tuberculosis, may be detected by the colorimetric sensor array by sampling a predetermined quantity of the trailing portion of the exhaled breath that is directed through the array at a predetermined flow rate. Other respiratory diseases can also be detected, again by sampling a predetermined quantity of the exhaled breath in a portion of the breath cycle, and by directing the sampled quantity at a predetermined flow rate through the array. The bacteria need not be entrained in exhaled breath, but, for example, can be entrained in a carrier gas that is passed through medical equipment whose sanitary condition is to be determined.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing," or any other variation thereof, are intended to cover a non-exclusive inclusion, such that a process, method, article, or apparatus that comprises, has, includes, or contains a list of elements does not include only those elements, but may include other elements not expressly listed or inherent to such process, method, article, or apparatus. An element proceeded by "comprises . . . a," "has . . . a," "includes . . . a," or "contains . . . a," does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially," "essentially," "approximately," "about," or any other version thereof, are defined as being close to as understood by one of ordinary skill in the art, and in one non-limiting embodiment the term is defined to be within 10%, in another embodiment within 5%, in another embodiment within 1%, and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. An apparatus for detecting an upper respiratory bacterial infection from exhaled mammalian breath, comprising:
    a colorimetric sensor array including a plurality of chemoresponsive colorants having a spectral response characteristic that changes when exposed to bacteria-produced analytes in the exhaled mammalian breath;
    a flow regulating system for directing a leading portion of the exhaled mammalian breath along a flow path into gaseous communication with the chemoresponsive colorants of the colorimetric sensor array to change the spectral response characteristic, and for discharging a trailing portion of the exhaled mammalian breath away from gaseous communication with the colorimetric sensor array exteriorly of the apparatus;
    an oxidizer upstream of the chemoresponsive colorants in the flow path for oxidizing the bacteria-produced analytes and increasing reactivity of the oxidized bacteria-produced analytes with the chemoresponsive colorants; and
    a spectral analysis system for analyzing the spectral response characteristic changed solely by the leading portion of the exhaled mammalian breath, and for detecting the upper respiratory bacterial infection when the bacteria-produced analytes are present therein.

2. The apparatus of claim 1, wherein the colorimetric sensor array has a plurality of separate flow channels, each channel having a plurality of the chemoresponsive colorants therein; and wherein the leading portion of the exhaled mammalian breath is directed along each channel.

3. The apparatus of claim 2, wherein the chemoresponsive colorants in at least one of the channels is located at a downstream portion of the one channel, wherein the oxidizer is located at an upstream portion of the one channel for oxidizing the bacteria-produced analytes and increasing reactivity of the bacteria-produced analytes with the chemoresponsive colorants in the one channel.

4. The apparatus of claim 3, wherein the oxidizer is one of sulfochromic acid and iodine pentoxide.

5. The apparatus of claim 2, wherein the chemoresponsive colorants in at least one of the channels is located at a downstream portion of the one channel, and a heater at an upstream portion of the one channel for heating the bacteria-produced analytes and increasing reactivity of the heated bacteria-produced analytes with the chemoresponsive colorants in the one channel.

6. The apparatus of claim 2, wherein the chemoresponsive colorants in a pair of the channels are located at respective downstream portions of the pair, and another oxidizer different from the first-mentioned oxidizer, where the different oxidizers are located at respective upstream portions of the pair for differently oxidizing the bacteria-produced analytes and differently increasing reactivity of the bacteria-produced analytes with the chemoresponsive colorants in the pair.

7. The apparatus of claim 2, wherein the flow regulating system includes a plurality of flow meters for capturing a predetermined volume of the leading portion of the exhaled mammalian breath, and a plurality of pumps for pumping the captured predetermined volume of the leading portion of the exhaled mammalian breath at a predetermined flow rate along each channel.

8. The apparatus of claim 1, wherein the flow regulating system includes a filter for filtering inhaled ambient air prior to exhalation.

9. The apparatus of claim 1, wherein the chemoresponsive colorants have a color characteristic that changes when exposed to the bacteria-produced analytes in the exhaled mammalian breath; and wherein the spectral analysis system includes an illuminator for illuminating the colorants with one of visible light, ultraviolet light and infrared light, and a color analyzer for comparing illuminated colors of the colorants before and after exposure to the bacteria-produced analytes.

10. A method of detecting an upper respiratory bacterial infection from exhaled mammalian breath in an apparatus, comprising:

directing only a leading portion of the exhaled mammalian breath along a flow path into gaseous communication with a plurality of chemoresponsive colorants of a colorimetric sensor array to change a spectral response characteristic of the array when the array is exposed to bacteria-produced analytes in the exhaled mammalian breath;

discharging a trailing portion of the exhaled mammalian breath away from gaseous communication with the colorimetric sensor array exteriorly of the apparatus;

in easing reactivity of the bacteria-produced analytes with the chemoresponsive colorants by oxidizing the bacteria-produced analytes with an oxidizer upstream of the chemoresponsive colorants in the flow path;

analyzing the spectral response characteristic changed solely by the leading portion of the exhaled mammalian breath with an analyzer; and detecting the upper respiratory bacterial infection when the bacteria-produced analytes are present therein.

11. The method of claim 10, and configuring the colorimetric sensor array with a plurality of separate flow channels, each having the plurality of chemoresponsive colorants therein; and wherein the directing is performed by directing the leading portion of the exhaled mammalian breath along each channel.

12. The method of claim 11, and locating the chemoresponsive colorants in at least one of the channels at a downstream portion of the one channel, wherein the oxidizing is performed by oxidizing the bacteria-produced analytes at an upstream portion of the one channel and increasing reactivity of the oxidized bacteria-produced analytes with the chemoresponsive colorants in the one channel.

13. The method of claim 12, wherein the oxidizing is performed by one of sulfochromic acid and iodine pentoxide.

14. The method of claim 11, and locating the chemoresponsive colorants in at least one of the channels at a downstream portion of the one channel, and heating the bacteria-produced analytes at an upstream portion of the one channel and increasing reactivity of the heated bacteria-produced analytes with the chemoresponsive colorants in the one channel.

15. The method of claim 11, and locating the chemoresponsive colorants in a pair of the channels at respective downstream portions of the pair, and differently oxidizing the bacteria-produced analytes with a pair of different oxidizers at respective upstream portions of the pair to differently increase reactivity of the bacteria-produced analytes with the chemoresponsive colorants in the pair.

16. The method of claim 11, and capturing a predetermined volume of the leading portion of the exhaled mammalian breath, and pumping the captured predetermined volume of the leading portion of the exhaled mammalian breath at a predetermined flow rate along each channel.

17. The method of claim 10, and filtering inhaled ambient air prior to exhalation.

18. The method of claim 10, and configuring the colorimetric sensor array with the plurality of chemoresponsive colorants whose color characteristic changes when exposed to the bacteria-produced analytes in the exhaled mammalian breath; and wherein the analyzing is performed by illuminating the colorants with one of visible light, ultraviolet light and infrared light, and by comparing illuminated colors of the colorants before and after exposure to the bacteria-produced analytes.

* * * * *